United States Patent
Sasaki et al.

(10) Patent No.: US 9,345,555 B2
(45) Date of Patent: May 24, 2016

(54) VISCOUS MATERIAL CONTAINER WITH EXPANDABLE BEND

(71) Applicant: SHOFU INC., Kyoto-shi, Kyoto (JP)

(72) Inventors: Tsukasa Sasaki, Soka (JP); Ryouji Takei, Soka (JP); Toshiyuki Nakatsuka, Kyoto (JP); Katsuya Kimoto, Kyoto (JP); Hideto Kasaba, Kyoto (JP)

(73) Assignee: SHOFU INC., Kyoto-Shi (JP)

( * ) Notice: Subject to any disclaimer, the term of this patent is extended or adjusted under 35 U.S.C. 154(b) by 0 days.

(21) Appl. No.: 14/224,174

(22) Filed: Mar. 25, 2014

(65) Prior Publication Data
US 2015/0093715 A1 Apr. 2, 2015

(30) Foreign Application Priority Data
Sep. 30, 2013 (JP) .................................. 2013-205446

(51) Int. Cl.
| B67D 7/60 | (2010.01) |
| G01F 11/00 | (2006.01) |
| A61C 5/04 | (2006.01) |
| A61C 5/06 | (2006.01) |
| A61C 1/12 | (2006.01) |

(52) U.S. Cl.
CPC ... A61C 5/04 (2013.01); A61C 1/12 (2013.01); A61C 5/062 (2013.01); A61C 5/066 (2013.01)

(58) Field of Classification Search
CPC ............ A61C 5/062; A61C 5/04; A61C 1/12; A61C 5/066
USPC ............................................ 222/386; 433/90
See application file for complete search history.

(56) References Cited

U.S. PATENT DOCUMENTS

| 5,445,523 A | 8/1995 | Fischer et al. |
| 5,707,234 A * | 1/1998 | Bender ........................... 433/90 |
| 5,848,894 A * | 12/1998 | Rogers ............................ 433/90 |
| 5,938,439 A | 8/1999 | Mertins et al. |
| 6,261,094 B1 * | 7/2001 | Dragan ........................... 433/90 |
| 6,379,152 B1 * | 4/2002 | Dragan ........................... 433/90 |
| 8,556,870 B2 * | 10/2013 | Fundingsland et al. ....... 604/311 |
| 2002/0076671 A1 * | 6/2002 | Evers et al. ..................... 433/90 |
| 2004/0152041 A1 * | 8/2004 | Metzbower ..................... 433/90 |

(Continued)

FOREIGN PATENT DOCUMENTS

| EP | 0397589 A1 | 11/1990 |
| EP | 1340472 A1 | 9/2003 |

(Continued)

OTHER PUBLICATIONS

European Search Report dated Jan. 15, 2015, 10 pages.

*Primary Examiner* — Patrick M Buechner
*Assistant Examiner* — Jeremy W Carroll
(74) *Attorney, Agent, or Firm* — Rankin, Hill & Clark LLP

(57) ABSTRACT

Provided herein is a viscous material container that is not likely to form continuous streaks or asperities on the surface of a viscous material discharged from the viscous material container even if the viscous material is highly viscous. A third section of a housing includes a wall having a wall portion that is positioned radially outwardly of a continuous angular portion with respect to a second imaginary center line, and extends along the continuous angular portion. The wall portion is configured to expand radially outward when a dental viscous material pushed out from a discharge port.

4 Claims, 5 Drawing Sheets

(56) References Cited

U.S. PATENT DOCUMENTS

2005/0147939 A1* 7/2005 Zumkeller ............... 433/90
2006/0204924 A1* 9/2006 Galehr et al. ............ 433/90
2012/0028217 A1* 2/2012 Spreizer .................. 433/90
2013/0032241 A1   2/2013 Yamaguchi et al.
2013/0134188 A1* 5/2013 Terakawa et al. ....... 222/386

FOREIGN PATENT DOCUMENTS

| | | |
|---|---|---|
| JP | 08-089515 A | 4/1996 |
| JP | 2003-250815 | 9/2003 |
| JP | 2012-071110 | 4/2012 |
| WO | 03/005927 A1 | 1/2003 |
| WO | 2011/132714 A1 | 10/2011 |

* cited by examiner

VISCOUS MATERIAL CONTAINER WITH EXPANDABLE BEND

TECHNICAL FIELD

The present invention relates to a viscous material container configured to contain a viscous material with a high viscosity and discharge an appropriate amount of the viscous material.

BACKGROUND ART

In treating a dental viscous material with a high viscosity such as a dental filling material, an artificial tooth material, and a tooth crown material in the dental field, a viscous material container such as a dental viscous material container that is a disposable container filled with the dental viscous material is used. The dental viscous material container is set onto a dedicated pushing device with a handle, and the handle of the pushing device is operated to discharge an appropriate amount of the dental viscous material from the dental viscous material container.

JP2012-071110A describes an example of conventional viscous material containers. The viscous material container includes a housing including a first section, a second section, and a third section. The first section has an insertion port at an end thereof, and includes a first inner wall surface configured to surround a first passage. The second section has a discharge port at an end thereof, and includes a second inner wall surface configured to surround a second passage. The third section is positioned between the first section and the second section, and includes a third inner wall surface configured to surround a third passage communicating with the first passage and the second passage. The viscous material container also includes an angular portion formed at a boundary portion between the second inner wall surface and the third inner wall surface.

SUMMARY OF INVENTION

Technical Problem

With the structure of the viscous material container described in JP2012-071110A, however, continuous streaks or asperities may be formed on the surface of the discharged viscous material if the viscous material is highly viscous. FIGS. 8A and 8B are photographs illustrating how the continuous asperities are actually formed. FIG. 8A is a photograph illustrating the continuous streaks or asperities appearing on the surface of the viscous material discharged from the viscous material container according to the related art as seen from a side. FIG. 8B is a photograph illustrating a part (upper left) of FIG. 8A as enlarged. When a viscous material with such continuous streaks or asperities is injected into a predetermined space, air bubbles may intrude into the space because of the presence of the streaks or asperities. In the dental field, in particular, intrusion of such air bubbles may change the apparent color of the viscous material or cause growth of bacteria from the air bubbles.

It is an object of the present invention to provide a viscous material container that is unlikely to form continuous streaks or asperities on the surface of a viscous material discharged from the viscous material container even if the viscous material is highly viscous.

Solution to Problem

As a result of the studies by the inventors, the inventors found that the cause of continuous streaks or asperities formed on the surface of the discharged viscous material if the viscous material is highly viscous lies in the angular portion formed at the boundary portion between the second inner wall surface and the third inner wall surface. The present invention has been made on the basis of such a finding. The present invention improves a viscous material container including a housing and a piston. The housing includes a first section, a second section, and a third section. The first section has an insertion port at an end thereof, and includes a first inner wall surface configured to surround a first passage extending along a first imaginary center line from the insertion port and having a transverse sectional shape that is circular about the first imaginary center line. The second section has a discharge port at an end thereof, and includes a second inner wall surface configured to surround a second passage extending along a second imaginary center line from the discharge port and having a transverse sectional shape that is circular about the second imaginary center line. The second imaginary center line intersects the first imaginary centerline. The third section is positioned between the first section and the second section, and includes a third inner wall surface configured to surround a third passage communicating with the first passage and the second passage. The piston is operable to move inside at least the first passage to push out a viscous material, which is contained in the first passage, from the discharge port through the second and third passages. The viscous material container also includes a continuous angular portion formed at a boundary portion between the second inner wall surface and the third inner wall surface. The continuous angular portion extends in a circumferential direction with respect to an angular portion located in an imaginary surface including the first imaginary center line and the second imaginary center line. The angular portion has an angle equal to an intersection angle between the first imaginary center line and the second imaginary center line.

In the viscous material container structured as described above, continuous streaks or asperities are formed on the surface of the discharged viscous material presumably because there is a large difference between the pressure applied to a portion of the viscous material at a position facing the angular portion and the pressure applied to a portion of the viscous material at a position opposite to the angular portion when the viscous material is discharged. It is presumed that such a large pressure difference caused around the viscous material results in repeated behavior in which the viscous material strongly contacts the angular portion and is displaced away from the angular portion. Thus, in the present invention, in order to reduce the effect of a large pressure difference caused by the presence of the continuous angular portion formed at the boundary portion between the second inner wall surface and the third inner wall surface, the housing includes a wall having a wall portion that is positioned radially outwardly of the continuous angular portion with respect to the second imaginary center line, and extends along the continuous angular portion, and the wall portion is configured to expand radially outward when the viscous material is pushed out from the discharge port.

If such a wall portion configured to expand radially outward upon application of a pressure from the viscous material is formed, the pressure difference discussed earlier caused when the viscous material is pushed out is reduced, thereby reducing occurrence of the behavior discussed earlier. When the viscous material with a high viscosity is pushed against the continuous angular portion, the continuous angular portion is deformed such that the interior angle of the continuous angular portion is increased to reduce the effect of the continuous angular portion. As a result, it is possible to effectively suppress continuous streaks or asperities formed on the surface of the discharged viscous material.

In a preferred embodiment of the present invention, the intersection angle between the first imaginary center line and the second imaginary center line is an angle in a range of 130 degrees±15 degrees. Such an intersection angle makes it possible to easily place the discharge port at a predetermined position in the oral cavity of a patient in the dental field, for example. If the intersection angle is in the range of 130 degrees±15 degrees, the angular range over which the expandable wall portion extends in the circumferential direction is 180 degrees or less in design.

If the intersection angle is in the angular range discussed earlier, the effect of the present invention is effectively achieved if the viscous material has a value of flowability in a range of 14.5 mm to 17.5 mm. The value of flowability as used herein is a value measured according to a predetermined flowability measuring method to be discussed later.

The housing may be unitarily molded from a resin material. In this case, the wall portion of the housing positioned radially outwardly of the continuous angular portion discussed earlier with respect to the second imaginary center line is preferably formed to have a thickness that is smaller than that of a portion of the wall in the vicinity of the wall portion. If the wall portion is formed in this way, the strength of the wall portion is lower than that of other portions of the wall so that only the wall portion expands radially outward.

Further, if the housing is unitarily molded from a resin material, the wall portion of the housing positioned radially outwardly of the continuous angular portion with respect to the second imaginary center line may be formed with a recessed portion extending in the circumferential direction with respect to a position at which the wall portion intersects the imaginary surface discussed earlier. This allows the wall portion to have a small thickness so that the wall portion expands radially outward. The recessed portion preferably extends in the circumferential direction, opens radially outward, and has an arcuate sectional shape as seen in the circumferential direction. If such a recessed portion is formed, the wall portion can have a thickness that is smaller than that of a portion of the wall in the vicinity of the wall portion. This allows the wall portion to expand radially outward such that the interior angle of the continuous angular portion is smoothly increased by a pressure applied when the viscous material with a high viscosity is pushed out. If the wall portion smoothly expands radially outward, the pressure difference is quickly reduced. This reliably prevents formation of asperities on the surface of the discharged viscous material.

If the resin material forming the housing is polypropylene, an opening portion of the recessed portion may have a width of 1.0 mm or more and 3.0 mm or less; the recessed portion may have a length in the circumferential direction of 5.0 mm or more and 8.0 mm or less; and the wall portion may have a thickness of 0.5 mm or more and 0.9 mm or less at a position corresponding to a bottom portion of the recessed portion, and the wall portion of the housing positioned radially outwardly of the continuous angular portion with respect to the second imaginary center line may be formed to have a maximum thickness of 0.7 mm or less. If the dimensions of the various portions are determined in this way, only the wall portion expands radially outward when the viscous material with a high viscosity is pushed out. This makes it possible to prevent breakage of the wall portion and leakage of the viscous material to the outside from the wall portion.

The housing preferably does not transmit visible rays. This allows use of a photocurable viscous material.

BRIEF DESCRIPTION OF DRAWINGS

FIG. 3 is a cross-sectional view taken along the line A-A of FIG. 1 with a piston pushed in.

DESCRIPTION OF EMBODIMENTS

An embodiment in which the present invention is applied to a dental viscous material container as a type of a viscous material container will be described below with reference to the drawings.

Figure 1:
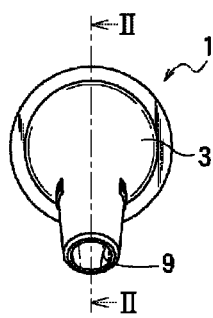
FIG. 1 is a front view of a dental viscous material container as a type of a viscous material container according to an embodiment of the present invention.
Figure 2:
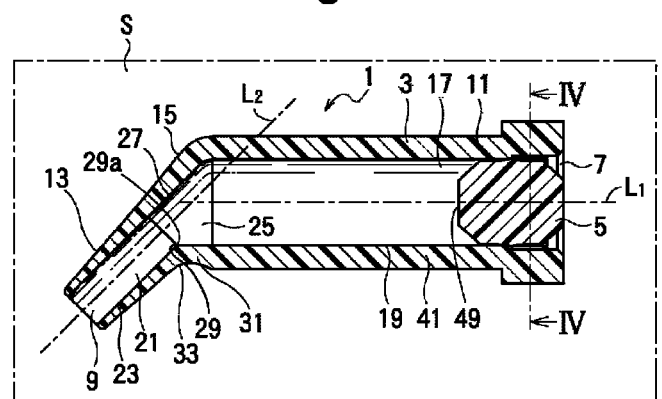
FIG. 2 is a cross-sectional view taken along the line A-A of FIG. 1.
Figure 3:
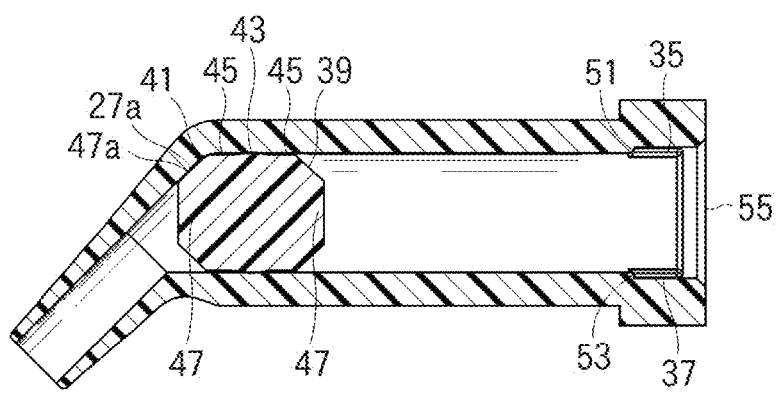
Figure 4:
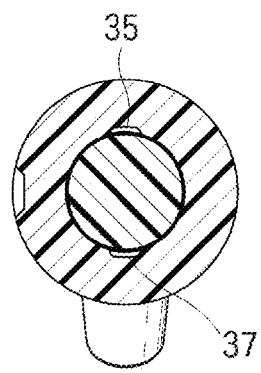
FIG. 4 is a cross-sectional view taken along the line B-B of FIG. 2.

FIG. 1 is a front view of a dental viscous material container 1 according to an embodiment of the present invention. FIG. 2 is a cross-sectional view taken along the line A-A of FIG. 1. FIG. 3 is a cross-sectional view taken along the line A-A of FIG. 1 with a piston pushed in. FIG. 4 is a cross-sectional view taken along the line B-B of FIG. 2. The dental viscous material container 1 has a housing 3 configured to house a dental viscous material (not illustrated) and a piston 5 operable to push out the dental viscous material. The housing 3 and the piston 5 are each unitarily formed from the same resin material. Examples of the resin material include polyethylene, polyacetal, polypropylene, polyamide, vinyl chloride resins, nylon, phenol resins, polyurethane, saturated polyester resins, melamine resins, polyvinylidene chloride, unsaturated polyester resins, polybutadiene, polystyrene, EVA (ethylene-vinyl acetate copolymer) resins, styrol resins, polymethylpentene, methacrylic styrene, ABS (acrylonitrile butadiene styrene) resins, and polycarbonate. In the embodiment, polypropylene is used. The housing 3 is formed using a material that does not transmit visible rays. Consequently, even if a photocurable dental viscous material is housed in the housing 3, it is possible to prevent the dental viscous material from being cured during storage.

The housing 3 includes an insertion port 7 into which the piston 5 is inserted and to which a dedicated pushing device (not illustrated) with a handle is to be connected, and a discharge port 9 from which the dental viscous material is discharged. The housing 3 includes a first section 11 having the insertion port 7 at an end thereof, a second section 13 having the discharge port 9 at an end thereof, and a third section 15 positioned between the first section 11 and the second section 13. The first section 11 includes a first inner wall surface 19 configured to surround a first passage 17 extending along a first imaginary center line L1 from the insertion port 7 and having a transverse sectional shape that is circular about the first imaginary center line L1. The second section 13 includes a second inner wall surface 23 configured to surround a second passage 21 extending along a second imaginary center line L2 from the discharge port 9 and having a transverse sectional shape that is circular about the second imaginary center line L2. The second imaginary center line L2 intersects the first imaginary center line L1. The third section 15 includes a third inner wall surface 27 configured to surround a third passage 25 communicating with the first passage 17 and the second passage 21.

The dental viscous material container 1 also includes a continuous angular portion 29 formed at a boundary portion between the second inner wall surface 23 and the third inner wall surface 27 to extend over a predetermined angular range. The continuous angular portion 29 extends in the circumferential direction with respect to an angular portion 29a located in an imaginary surface S including the first imaginary center line L1 and the second imaginary center line L2. The angular portion 29a has an angle equal to an intersection angle between the first imaginary center line L1 and the second imaginary center line L2. In the embodiment, the intersection angle is 135 degrees. The angle of the continuous angular portion 29 becomes larger as it extends in the circumferential direction with respect to the angular portion 29a. The predetermined angular range over which the continuous angular portion 29 extends in the circumferential direction is difficult to clearly specify from actual products, but is 180 degrees or less in design.

In particular, if the intersection angle between the first imaginary center line L1 and the second imaginary center line L2 is an angle in the range of 130 degrees±15 degrees, it is possible to easily place the discharge port 9 at a predetermined position in the oral cavity of a patient.

The housing 3 includes a wall having a wall portion 31 that is positioned radially outwardly of the continuous angular portion 29 with respect to the second imaginary center line L2, and extends along the continuous angular portion 29. The wall portion 31 is configured to expand radially outward when the dental viscous material is pushed out from the discharge port 9. Specifically, as described later, the wall portion 31 is formed to have a thickness that is smaller than that of a portion of the wall in the vicinity of the wall portion 31 so that only the wall portion 31 expands radially outward.

If such a wall portion configured to expand radially outward upon application of a pressure from the viscous material is formed along the continuous angular portion 29, the pressure difference discussed earlier caused when the viscous material is pushed out is reduced, thereby reducing occurrence of behavior of the viscous material such as strong contact against the continuous angular portion 29 and displacement away from the continuous angular portion 29. When the viscous material with a high viscosity is pushed against the continuous angular portion 29, the continuous angular portion 29 is deformed such that the interior angle of the continuous angular portion 29 is increased to reduce the effect of the continuous angular portion 29. As a result, it is possible to effectively suppress continuous streaks or asperities formed on the surface of the discharged viscous material.

In the embodiment, the wall portion 31 is formed to have a thickness that is smaller than that of a portion of the wall in the vicinity of the wall portion 31 so that only the wall portion 31 expands radially outward. Specifically, the wall portion 31 is formed with a recessed portion 33 extending in the circumferential direction with respect to a position at which the wall portion 31 intersects the imaginary surface S (a position corresponding to the angular portion 29a), and the recessed portion 33 opens radially outward and has an arcuate sectional shape as seen in the circumferential direction. If such a recessed portion 33 is formed, the wall portion 31 can have a thickness that is smaller than that of a portion of the wall of the third section 15 other than the wall portion 31. This allows the wall portion 31 to expand radially outward such that the interior angle of the continuous angular portion 29 is smoothly increased by a pressure applied when the dental viscous material is pushed out.

In the embodiment, the effect of the present invention is effectively achieved if the viscous material has a value of flowability in the range of 14.5 mm to 17.5 mm. A dental filling material used as the dental viscous material has a value of flowability in the range of 15.2 mm to 16.8 mm. The term "value of flowability" of the viscous material as used herein is defined as follows. In the specification, the flowability of each viscous material is measured five times by the following method, and the average of the five measured values is obtained as the "value of flowability" of each viscous material.

(1) A cylindrical glass tube (inside diameter: 7.5 mm) inserted into a glass tube fixing platform, and a spacer and a cellophane sheet (disc-shaped) are sequentially inserted from the upper portion of the cylindrical glass tube to assemble a measuring instrument.

(2) A sample is injected into a paste injecting portion (volume: 309 $mm^3$) at the upper portion of the cylindrical glass tube (inside diameter: 7.5 mm) with no intrusion of air bubbles, and the upper surface of the injected sample is flattened according to the shape of the cylindrical glass tube using a plastic spatula.

(3) The glass tube is taken out, and a glass bar is inserted into the glass tube from the side opposite to the injecting portion to push out the sample gently onto a glass plate of 50×50×1 mm.

(4) The glass plate is moved to a loader, and a glass plate of the same size is placed on the sample and a weight (385 gf) of the loader is gently applied at the same time. The sample is left to stand for three minutes. After three minutes, the weight is removed, and the distance between two parallel tangents to the sample spread between the glass plates is measured at two points using plotting paper. The distances obtained at the two points are determined as A mm and B mm, and the value of flowability is calculated by the following formula:

$$\text{Value of flowability} = (A+B)/2 \text{ (mm)}$$

The first section 11 is formed with two groove portions 35 and 37 communicating with the first passage 17 to discharge air in the first passage 17 when the piston 5 is inserted from the insertion port 7. The two groove portions 35 and 37 communicate with the insertion port 7, and extend along the first imaginary center line L1. The length of the groove portions 35 and 37 along the first imaginary center line L1 and the length of a non-contact portion 39 of the piston 5 to be discussed later are determined such that air in the housing 3 is discharged out of the housing 3 through the groove portions 35 and 37 until the piston 5 is inserted into the first passage 11 to the extent that an annularly circular contact portion 43 of the piston 5 goes beyond the groove portions 35 and 37. If the groove portions 35 and 37 are formed in this way, air in the first passage 17 can be guided to the groove portions 35 and 37 when the piston 5 is inserted from the insertion port 7. Consequently, air in the housing 3 can be reliably discharged. In the embodiment, two groove portions are formed. However, it is a matter of course that one or three or more groove portions may be formed as long as air in the housing 3 can be reliably discharged.

Figure 5:
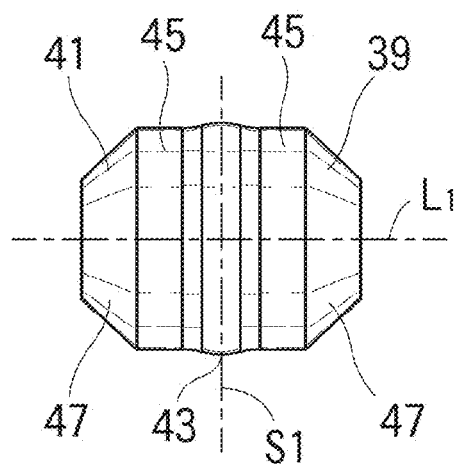
FIG. 5 is a side view of the piston according to the embodiment of the present invention.
Figure 6:
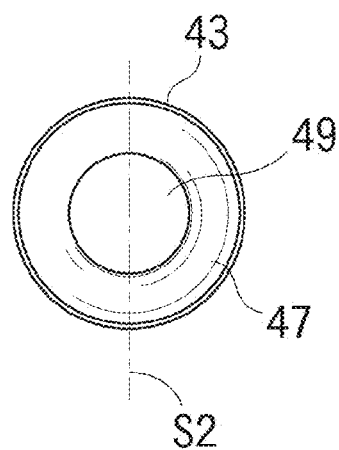
FIG. 6 is a front view of the piston.
Figure 7:
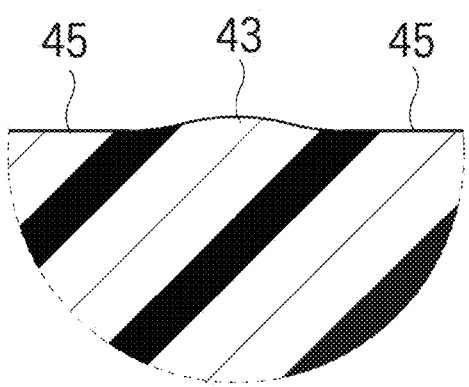
FIG. 7 is a cross-sectional view of the piston taken along a second imaginary surface, illustrating a part of an annularly circular contact portion and the surroundings thereof as enlarged.
Figure 8A:
FIG. 8A is a photograph illustrating continuous streaks or asperities appearing on the surface of a viscous material discharged from a viscous material container according to the related art as seen from a side.
Figure 8B:
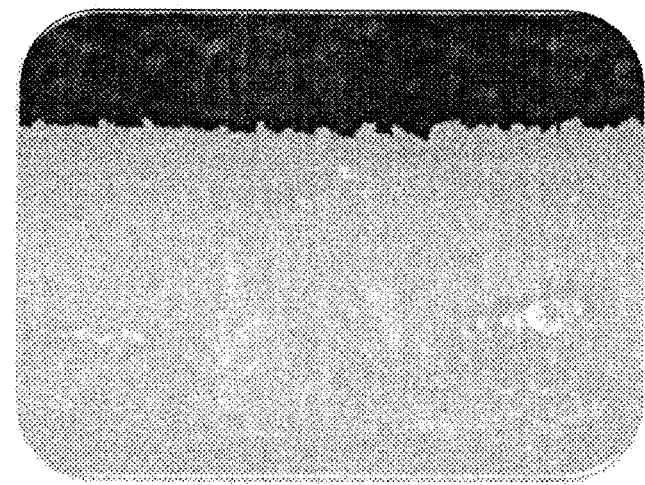
FIG. 8B is a photograph illustrating a part (upper left) of FIG. 8A as enlarged.

Next, the shape of the piston 5 will be described. FIG. 5 is a side view of the piston 5. FIG. 6 is a front view of the piston 5. FIG. 7 is a cross-sectional view of the piston 5 taken along the second imaginary surface S2, illustrating a part of the annularly circular contact portion 43 and the surroundings thereof as enlarged. The piston 5 includes the annularly circular contact portion 43 and a pair of non-contact portions 39 and 41. The annularly circular contact portion 43 contacts the first inner wall surface 19 as the piston 5 is inserted in the first passage 17. The pair of non-contact portions 39 and 41 do not contact the first inner wall surface 19 as the piston 5 is inserted in the first passage 17, located at both sides of the annularly circular contact portion 43 in the direction of extension of the first imaginary center line L1 and having an outside diameter that is smaller than that of the annularly circular contact portion 43. If the piston 5 is provided with the pair of non-contact portions 39 and 41, the piston 5 can be temporarily arranged during insertion. Further, if the pair of non-contact portions 39 and 41 are shaped to be plane-symmetric, the piston 5 can be inserted from the insertion port 7 from either non-contact portion side. The area of contact between the piston 5 and the housing 3 is small. Therefore, even if the housing 3 and the piston 5 are each unitarily formed from the same resin material, the piston 5 still can slide smoothly.

The pair of non-contact portions 39 and 41 each have an annular non-contact surface 45 that is adjacent to the annularly circular contact portion 43. The annular non-contact surface 45 has a diameter that is 90% or more of that of the first inner wall surface 19. If the annular non-contact surfaces 45 are formed in this way, the annular non-contact surfaces 45 can be fitted well in the first inner wall surface 19 to reliably temporarily arrange the piston 5. An end portion 47 of each of the pair of non-contact portions 39 and 41 is shaped to surface-contact the third inner wall surface 27 surrounding the third passage 25. If the shape of the end portion 47 of each of the pair of non-contact portions 39 and 41 is determined in this way, it is possible to discharge a larger amount of the dental viscous material without waste. In the embodiment, the end portion 47 is formed in a truncated conical shape. As illustrated in FIG. 3, a surface 27*a* of the third inner wall surface 27 on the upper side (the side facing the angular portion 29*a*) and a conical surface 47*a* of the end portion 47 on the upper side surface-contact each other with the piston 5 completely pushed toward the discharge port 9.

The distance between an end surface 49 of the piston 5 to be inserted into the first passage 17 and the annularly circular contact portion 43 is equal to the distance between respective end portions 51 and 53 of the groove portions 35 and 37 on the first passage 17 side and an end portion 55 of the first section 11 on the insertion port 7 side. Such a configuration allows air to be completely discharged when the piston 5 is completely inserted into the first passage 17. In addition, the pair of non-contact portions 39 and 41 are shaped such that the annularly circular contact portion 43 is positioned at a vertex of an arcuate shape when the piston 5 is cut along the second imaginary surface S2 which includes the first imaginary center line L1 and which is orthogonal to the first imaginary surface S1. If the pair of non-contact portions 39 and 41 are formed in this way, the area of contact between the piston 5 and the housing 3 can be reduced, which allows the dental viscous material to be pushed out with a small force.

EXAMPLE

An example was prepared to verify the effect of the embodiment. In the example, a dental viscous material with a value of flowability of 16.0 mm, which was the average of values obtained through five measurements conducted on the viscous material, was injected into a container. Polypropylene was used as the resin material to form the housing 3 and the piston 5. In this case, the housing 3 was formed such that: an opening portion of the recessed portion 33 had a width of 1.0 mm or more and 3.0 mm or less (in the embodiment, 1.5 mm); the recessed portion 33 had a length in the circumferential direction of 5.0 mm or more and 8.0 mm or less (in the embodiment, 6.5 mm); and the wall portion 31 had a thickness of 0.5 mm or more and 0.9 mm or less (in the embodiment, 0.65 mm) at a position corresponding to a bottom portion of the recessed portion 33. If the dimensions of the various portions were determined in this way, only the wall portion 31 expanded radially outward when the dental viscous material with a high viscosity was pushed out. This made it possible to prevent breakage of the wall portion 31 and leakage of the dental viscous material to the outside from the wall portion 31. It was visually observed that substantially no streaks or asperities were formed on the surface of the viscous material discharged from the discharge port 9.

In the embodiment described above, the housing 3 and the piston 5 are formed from the same material. However, it is a matter of course that the housing 3 and the piston 5 may be formed from different materials.

In the embodiment described above, the discharge port 9 is exposed. However, it is a matter of course that the third section 15 may be fitted with a cap configured to block the discharge port 9. In this case, an engagement structure may be provided between the outer peripheral portion of the third section 15 and the cap to prevent the cap from falling off.

In the embodiment described above, the recessed portion 33 is provided to constitute the wall portion 31 which expands radially outward. However, the wall portion 31 configured to expand radially outward upon application of a pressure from the viscous material may be formed from a material that is softer than a material forming other portions of the wall. In this case, the housing 3 may be formed by insert molding using an object for forming the wall portion 31 as an insert.

INDUSTRIAL APPLICABILITY

According to the present invention, a wall portion configured to expand radially outward upon application of a pressure from a viscous material is formed. Thus, the pressure difference caused when the viscous material is pushed out is reduced. When the viscous material with a high viscosity is pushed against the continuous angular portion, the continuous angular portion is deformed such that the interior angle of the continuous angular portion is increased to reduce the effect of the continuous angular portion. As a result, it is possible to effectively suppress continuous streaks or asperities formed on the surface of the discharged viscous material.

DESCRIPTION OF REFERENCE NUMERALS 1 dental viscous material container
3 housing
5 piston
7 insertion port
9 discharge port
11 first section
13 second section
15 third section
17 first passage
19 first inner wall surface
21 second passage
23 second inner wall surface 25 third passage
27 third inner wall surface
27a surface
29 continuous angular portion
29a angular portion
31 wall portion
33 recessed portion
35, 37 groove portion
39, 41 non-contact portion
43 annularly circular contact portion
45 annular non-contact surface
47 end portion
47a conical surface
49 end surface
51, 53 end portion
55 end portion
L1 first imaginary center line
L2 second imaginary center line
S imaginary surface
S1 first imaginary surface
S2 second imaginary surface

What is claimed is:

1. A viscous material container comprising:
a housing comprising:
a first section having an insertion port at an end thereof and including a first inner wall surface configured to surround a first passage extending along a first imaginary center line from the insertion port and having a transverse sectional shape that is circular about the first imaginary center line;
a second section having a discharge port at an end thereof and including a second inner wall surface configured to surround a second passage extending along a second imaginary center line from the discharge port and having a transverse sectional shape that is circular about the second imaginary center line, the second imaginary center line intersecting the first imaginary center line; and
a third section positioned between the first section and the second section and including a third inner wall surface configured to surround a third passage communicating with the first passage and the second passage;
a piston operable to move inside at least the first passage to push out a viscous material, which is contained in the first passage, from the discharge port through the second and third passages; and
a continuous angular portion formed at a boundary portion between the second inner wall surface and the third inner wall surface, the continuous angular portion extending in a circumferential direction with respect to an angular portion located on an inside surface of the housing in an imaginary surface including the first imaginary center line and the second imaginary center line, the angular portion having an angle equal to an intersection angle between the first imaginary center line and the second imaginary center line, wherein:
the housing includes a wall having a wall portion that is positioned radially outwardly of the continuous angular portion with respect to the second imaginary center line, and extends along the continuous angular portion, and the wall portion is configured to expand radially outward when the viscous material is pushed out from the discharge port,
the housing is unitarily molded from a resin material,
the wall portion has a thickness that is smaller than that of a portion of the wall in the vicinity of the wall portion,
the wall portion is formed with a recessed portion extending in the circumferential direction with respect to a position at which the wall portion intersects the imaginary surface, the recessed portion opening radially outward and having an arcuate sectional shape as seen in the circumferential direction,
the intersection angle between the first imaginary center line and the second imaginary center line is an angle in a range of 130 degrees±15 degrees,
the viscous material has a value of flowability in a range of 14.5 mm to 17.5 mm,
the resin material is polypropylene,
an opening portion of the recessed portion has a width of 1.0 mm or more and 3.0 mm or less,
the recessed portion has a length in the circumferential direction of 5.0 mm or more and 8.0 mm or less, and
the wall portion has a thickness of 0.5 mm or more and 0.9 mm or less at a position corresponding to a bottom portion of the recessed portion.

2. The viscous material container according to claim 1, wherein the continuous angular portion extends about the second imaginary center line.

3. The viscous material container according to claim 2, wherein the housing does not transmit visible rays.

4. The viscous material container according to claim 1, wherein the housing does not transmit visible rays.

* * * * *